United States Patent
Ratogi et al.

(10) Patent No.: US 6,881,582 B2
(45) Date of Patent: Apr. 19, 2005

(54) THIN FILM ETHANOL SENSOR AND A PROCESS FOR THE PREPARATION

(75) Inventors: Alok Chandra Ratogi, New Delhi (IN); Kiran Jain, New Delhi (IN); Heremba Prasad Gupta, New Delhi (IN); Vipin Kumar, New Delhi (IN)

(73) Assignee: Council of Scientific and Industrial Research, New Delhi (IN)

(*) Notice: Subject to any disclaimer, the term of this patent is extended or adjusted under 35 U.S.C. 154(b) by 187 days.

(21) Appl. No.: 10/045,472

(22) Filed: Nov. 8, 2001

(65) Prior Publication Data

US 2003/0087452 A1 May 8, 2003

(51) Int. Cl.⁷ .................................................. G01N 33/20
(52) U.S. Cl. ..................... 436/83; 436/127; 436/132; 556/64; 556/67
(58) Field of Search ............................... 436/127, 132, 436/83, 152; 422/84, 94, 98; 556/64, 67

(56) References Cited

U.S. PATENT DOCUMENTS

| | | | |
|---|---|---|---|
| 3,578,690 A | * 5/1971 | Becker | 554/71 |
| 4,504,420 A | * 3/1985 | Ebner | 558/321 |
| 4,587,104 A | * 5/1986 | Yannopoulos | 422/94 |
| 5,071,814 A | * 12/1991 | Sasaki et al. | 502/205 |
| 5,082,789 A | * 1/1992 | Morrison et al. | 436/132 |
| 5,252,140 A | * 10/1993 | Kobayashi et al. | 136/258 |

OTHER PUBLICATIONS

Hunger et al. Organometallics. "Syntheses of Heteronuclear Molybdenum/Bismuth Alkoxides Stabilized by Organic Ligands". pp. 1044–1050. Oct. 1999.*

* cited by examiner

Primary Examiner—Jill Warden
Assistant Examiner—LaToya Cross
(74) Attorney, Agent, or Firm—Harness Dickey & Pierce, P.L.C.

(57) ABSTRACT

Disclosed is a method of making a bismuth molybdate precursor solution using a metallorganic decomposition (MOD) process consisting of the formation of a precursor sol of hexanoates of Bismuth (Bi) and Molybdenum (Mo). The precursor solution is used to make thin film of Bismuth molybdate by spin coating and spray pyrolysis. The bismuth molybdate films have the useful alpha and gamma phases having high sensitivity to ethanol gas, the detection of the ethanol gas is based upon the change of electrical conductivity of a thick film of the semiconductor oxide sensing element resulting from the ethanol gas in an oxygen-containing atmosphere. When the drying is effected by spray pyrolysis, quite thick films with high adhesion have been produced over different substrates, including quartz. The thin film of the present invention made by spray pyrolysis has a very fast response to ethanol detection eg typically 5 seconds.

10 Claims, 4 Drawing Sheets

THIN FILM ETHANOL SENSOR AND A PROCESS FOR THE PREPARATION

FIELD OF THE INVENTION

The present invention relates to a sensitive, fast response thin film ethanol sensor. More particularly, the present invention relates to preparation of thin film of bismuth molybdate useful as an ethanol sensor. The present invention also refers to a process for the preparation of a precursor solution of bismuth molybdenum hexanoate for preparation of thin films of bismuth molybdate for ethanol sensing.

BACKGROUND OF THE INVENTION

Alcohol consumption is a commonplace during festivities and also it is rather common that people do take to driving under drunken state and pose real danger to passer by and of the vehicles. As per laws of almost all the countries there is highest permissible limit of alcohol concentration in humans while driving. Not only this, a drunken subject is a cause of nuisance while on job and is endangered while working on a machine. All these situations warrant measurement of presence of alcohol in humans to meet the legal requirements. This social and legal objective is met by use of means which help in detection of alcohol.

Conventional technology utilized for alcohol (also referred to herein as ethanol or ethyl alcohol, $CH_3CH_2OH$) detection in traffic and traffic related situations relies on two different approaches: Screening for blood alcohol is used to determine whether an individual's blood alcohol content (BAC) is below or above a certain threshold value. In most cases, screening is done by means of breath analysis to establish the breath alcohol content (BAC). Evidential blood alcohol testing is required to establish legally-binding BAC values and, normally, is required after a positive breath alcohol test result.

There are a number of technologies that are used for alcohol detection in gas samples. The various means used in most commercial breath analyzers are: a) Fuel Cells b) Semiconductors c) Infrared Absorption d) Gas Chromatography and (e) Calorimetry. The use of semiconducting oxides as gas sensors has been common for several years. The electrical resistance of such sensors has been found to vary in a predictable manner when the sensor is operated in the presence of a particular gas, or concentration of gas, thus facilitating detection of particular gases or gas concentrations. Due to its high importances, there is a continuous need to prepare better and faster selective sensor for ethanol gas so that it can be used to test alcohol concentration in drunken subjects. This need has prompted the investigation of new materials/preparation by better technique which can function as gas detecting elements and particularly as alcohol sensors.

Stannic oxide has been found to be a particularly useful semiconductor oxide for gas detection when it is mixed with small amounts of a noble metal catalyst such as platinum, palladium and rhodium. This is disclosed in a U.S. Pat. No. 4,592,967. This invention discloses a gas sensor adapted to ethyl alcohol and the like and maintained at about 300.degree. to 450.degree. C. The draw back here is in the use of cumbersome process of making a solid paste and subsequent application on a substrate followed by high temperature firing at about 800 C for two hours. The method has been referred to as a kneading process.

Reference may also be made to a U.S. Pat. No. 5,944,661 which discloses electrochemical solid polymer electrolyte sensor for continuous ethanol measurement. The invention describes the continuous measurement of transdermal alcohol by measurement of electromechanical ethanol oxidation current. The transdermal alcohol sensor (TAS) essentially comprises a sensor assembly consisting of three-electrode system for measuring electrical signals. These electrodes are thermally processed in oven at 300–350° C. for a time in the range of 15–60 minutes. All the three electrode have to be bonded to the solid polymer electrolyte membrane at typical processing conditions of time in the range of 15–60 minutes, a temperature in the range of 250–350° C. and a pressure of 600 to 1200 psi. The major drawback of the TAS is that it has to form an airtight contact with the skin and also preferably needs a perspiring skin to actually effect the alcohol concentration measurement. Further drawback is that, to get a meaningful measurement, the sensor has to be used to record data over an extended period of time from few hours to a few days.

Reference may be made to yet another U.S. Pat. No. 5,907,407 and the PCT application number PCT/US99/17770. This invention describes alcohol sensing on the basis of intracavity laser spectroscopy (ILS) mainly for measuring alcohol in a vehicle. This is also a good means to detect consumption of alcohol by subjects driving vehicles under drunken state. However, the invention suffers from the drawback that a laser system is needed to be used. Yet another shortcoming is that the detection of alcohol in a vehicle by this or any other means may not warrant any legal action as the presence of an ethanol vapour can arise due to many other reasons not under the control of the driver.

Reference may be made to the work by Morrison, et al. (U.S. Pat. No. 5,082,789, 1992) which shows that bismuth molybdate (a term which is hereinafter used to describe an oxide where bismuth and molybdenum are cations of various atomic percentages and oxygen is the anion) can be used as a gas sensor with good sensitivity for certain gases and good reproducibility and stability, and in particular almost zero dependence of the sensor characteristics (the electrical resistivity) on the relative humidity. The patent particularly describes Bismuth molybdate gas sensors useful for the detection of alcohol in the breath, having both substantial sensitivity in the concentration range of interest (200 ppm) and having negligible response to the humidity from the breath. Bismuth molybdate sensors have been prepared in thin film of material or as a sintered powder. However, the invention suffers from certain drawbacks namely; the film material as grown by thermal evaporation was oxygen deficient and had to be sintered at 400° C. for 4 hours to improve the conductivity suitable for alcohol detection. The turn on time in the invention is also on a higher side i.e. 10 minute for a concentration of 200 ppm. The sensor operates at a temperature of 340° C. Further, to increase the sensitivity of the sensor, the invention proposes to dope the samples with noble metals like platinum, silver or palladium. The patent further discloses that the optimum sensitivity is obtained when the sample is a mixture of both, the ↔ and ↕ phases of bismuth molybdate. This situation is surely not desirable, as the control of the amount of presence of the two phases will be rather tricky and difficult. This may result in irreproducible desired sensitivity for the sample to act as ethanol or gas sensor. All these drawbacks combined together render the sensor, described in the patent, costly to manufacture and also rather problematic in use when a higher temperature is required for actual use.

Till now in most of the work to prepare bismuth molybdate one of the two techniques are followed, in the first method the oxides of bismuth and molybdenum are dry mixed and heated (calcined) at high temperatures and reacted to form compound (called the solid state or ceramic route). In the second method Bismuth molybdate is formed from aqueous solution by co-precipitation of bismuth and molybdenum oxide from bismuth nitrate and ammonium heptamolybdate, by adjusting the pH of the solution as disclosed in a U.S. Pat. No. 5,082,792. To prepare films either vacuum evaporation technique is used or the thick film procedure have been applied.

The present invention circumvents all the drawbacks as mentioned above and is capable of easy adaptation in any small scale manufacturing environment To the best of our knowledge no patent exists on fabricating bismuth molybdate using metallorganic decomposition (MOD) route. The basic approach in MOD technique consists of simply dissolving the metal organic compound in a common solvent such as xylene and combing the solutions to yield the desired stoichiometry. Since the starting compounds are water insensitive, the solution retains proper stoichiometry. Once the deposition solution has been synthesized thin films can be prepared by known methods but other than evaporation techniques.

OBJECTS OF THE INVENTION

Main object of the present invention is to provide a process for the preparation of a sensitive, fast response thin film ethanol sensor.

Another object of the invention is to provide an improved method for the production of a low cost bismuth molybdate thin film sensor for detection of ethanol gas.

It is an object of the present invention to provide a stable precursor solution of bismuth molybdenum hexanoate for depositon of bismuth molybdate thin film useful for ethanol sensing.

Still another object of the present invention is to provide a metallorganic deposition technique for thin film preparation of bismuth molybdate without the need for post deposition anneal.

Yet another object of the present invention is to provide a method to prepare an ethanol sensor capable of working at reduced temperature.

It is a further object of the present invention to provide a semiconductor oxide material, which does not require the presence of any catalyst, useful as an ethanol sensor.

DESCRIPTION OF THE DRAWINGS

In the drawings accompanying the description.

Curve (a) represents Infra Red spectrum for '⊢⊣" phase bismuth molybdate.

Curve (b) represents IR spectrum for 'ℑ' phase bismuth molybdate.

Figure 1:
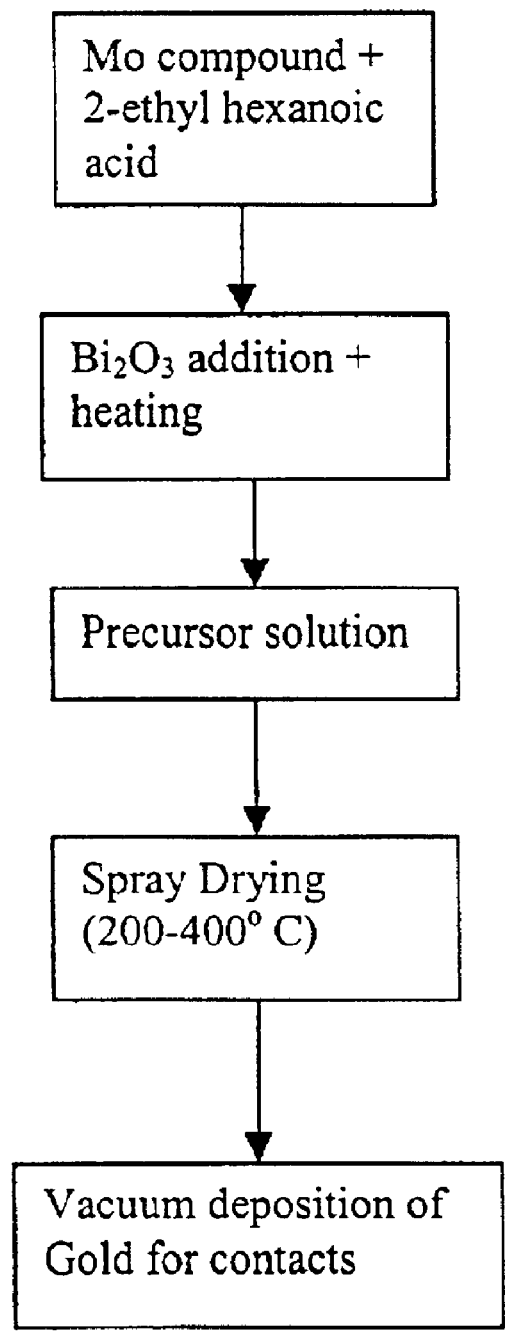
FIG. 1 represents different processing steps for fabricating thin film sensor element.
Figure 2:
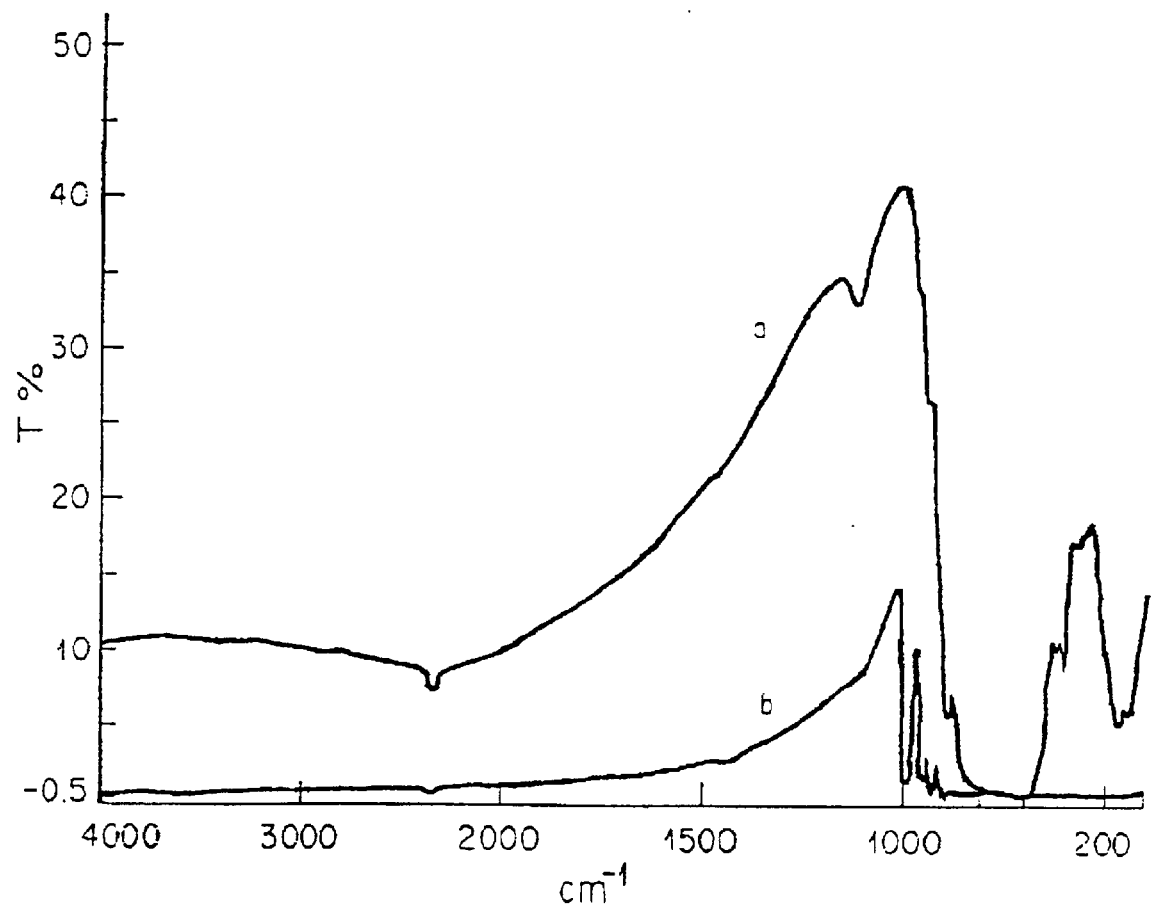
FIG. 2 shows Infra .Red (IR). spectra for alpha and beta phase of bismuth molybdate sample.
Figure 3:
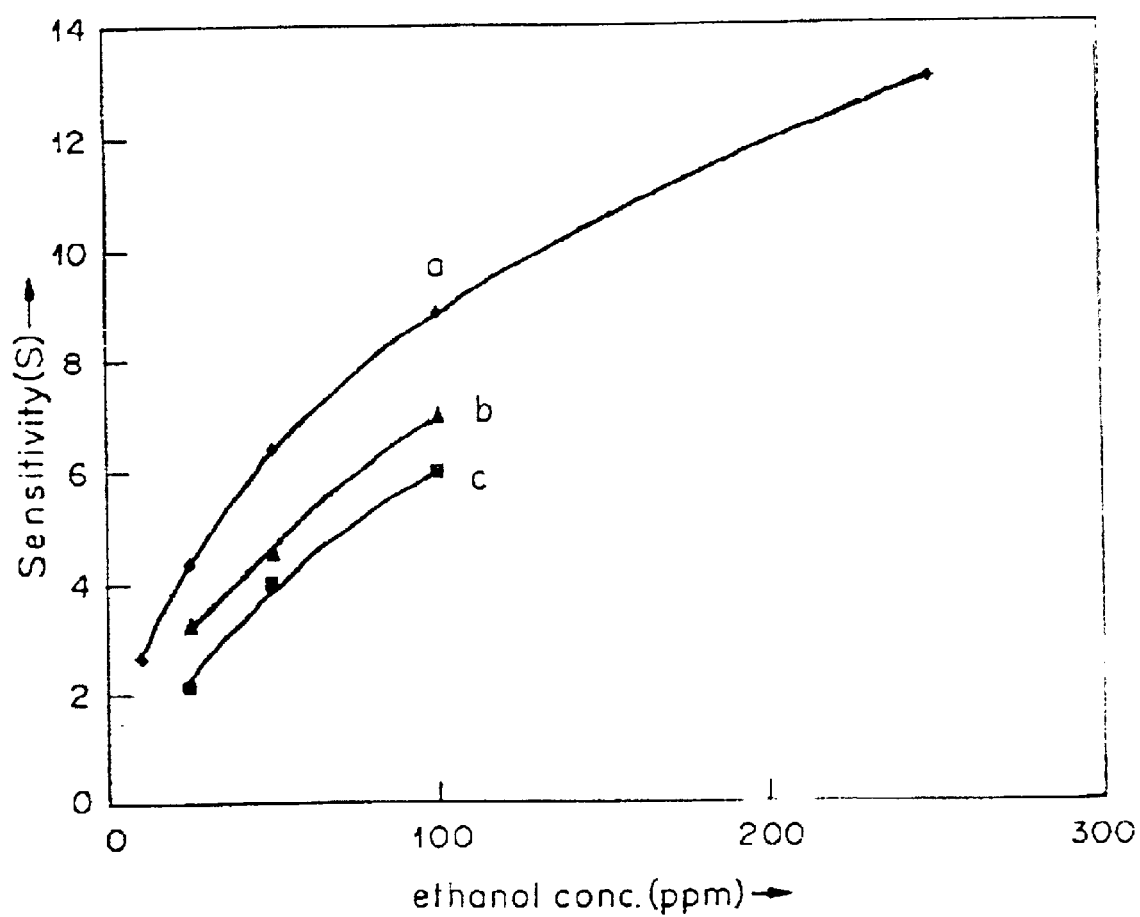

FIG. 3 represents the ethanol vapor sensitivity for various ethanol vapour concentrations at temperatures 275–325° C. for as deposited film consisting of alpha phase of bismuth molybdate by spray process. Here sensitivity is defined as a ratio of resistance in air $R_0$ divided by resistance in presence of ethanol vapor $R_g$ i.e. ($R_0/R_g$).

Curve (a) represents variation of sensitivity for sample temp. of 325° C.

Curve (b) represents variation of sensitivity for sample temp. of 300° C.

Curve (c) represents variation of sensitivity for sample temp. of 275° C.

Figure 4:
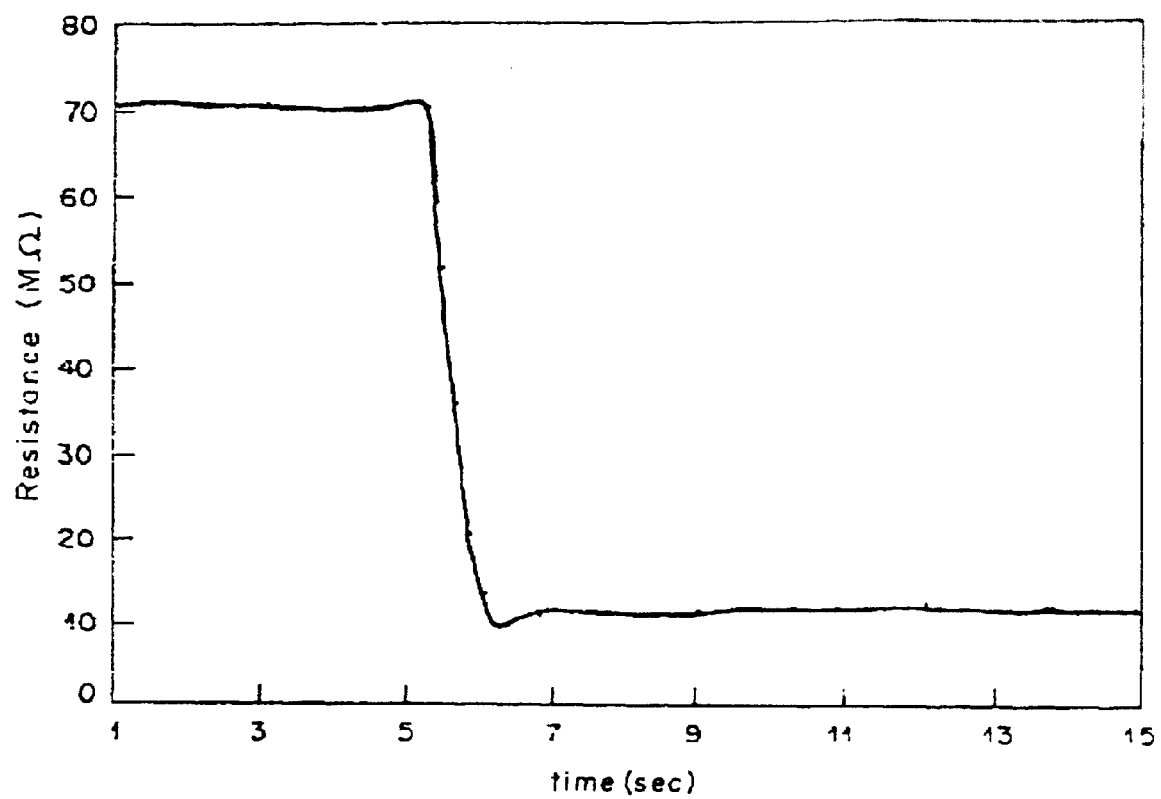

FIG. 4 represents the response i.e. resistance variation with time for alpha phase film when exposed to ethanol vapour

DETAILED DESCRIPTION OF THE INVENTION

Accordingly, the present invention provides a sensitive, fast response thin film ethanol sensor comprising a substrate coated with a thin film of bismuth molybdate and having electrode contacts deposited on said substrate coated with the thin film.

In an embodiment of the present invention the substrate may be selected from the group consisting of alumina, titania, zirconia, glass, quartz glass and silica.

In another embodiment of the present invention the thin film may have the ratio of bismuth to molybdenum as 2:2.

In a further embodiment of the present invention the thin film may have the ratio of bismuth to molybdenum as 2:3.

In a still further embodiment of the present invention, the electrode contacts are deposited by vacuum evaporation.

In an embodiment of the present invention, the evaporated electrode contacts are gold contacts.

In yet further embodiment of the present invention the thin film may be characterized by the ability to detect concentrations of at least 10 ppm of ethanol vapour in human breath.

In still further embodiment of the present invention the thin film may be characterized by change in resistance in at least 10 seconds due to human breath containing ethanol vapour.

In a further embodiment of the present invention the thin film may be characterized by change in resistance due to human breath containing ethanol vapours at a thin film temperature of 250° C.

In another embodiment of the present invention the sensitivity of the thin film ethanol sensor may be in the range of 2.0 to 14.5.

In still another embodiment of the present invention the stability of the thin film ethanol sensor may be at least for one year.

The present invention also provides a process for the preparation of a sensitive, fast response thin film ethanol sensor which comprises, depositing a thin film, from a precursor solution of bismuth molybdenum hexanoate solution, on a substrate at a temperature in the range of 200 to 400° C., cooling the deposited film, depositing electrode contacts on the said thin film ethanol sensor.

In an embodiment of the present invention the substrate may be selected from the group consisting of alumina, titania, zirconia, glass, quartz glass and silica In another embodiment of the present invention the ratio of bismuth cation to molybdenum cation in the precursor solution may be 2:2 to 2:3.

In another embodiment of the present invention, the thin film of Bismuth molybdate is deposited by known technique.

In a further embodiment of the present invention, the thin film of Bismuth molybdate is deposited by spray pyrolysis method.

In yet another embodiment of the present invention, the thin film spray deposition technique may be carried out with a chemically inert gas such as pure nitrogen gas.

In still another embodiment of the present invention the electrode contacts are deposited by vacuum evaporation.

In one more embodiment of the present invention, the electrode contacts are evaporated by thermal evaporation.

The present invention further provides a process for preparing precursor solution of bismuth molybdenum hexanoate said process comprising: dissolving molybdenum trioxide in oxalic acid solution, the said solution being concentrated to give a blue coloured solution, adding 2-ethyl hexanoic acid to said blue coloured solution, heating the resulting mixed solution to a temperature in the range of 100 to 150° C. for a period in the range of 30 to 60 minutes to remove water, said water free solution being maintained at a temperature in the range of 150 to 250° C. for a period in the range of 30 min to 90 minutes to obtain a hot brown coloured solution, adding bismuth trioxide slowly to the said brown coloured hot solution under reflux thereby getting bismuth molybdenum hexanoate precursor solution.

In an embodiment of the present invention, the purity of 2 ethyl hexanoic acid may be at least reagent grade.

In another embodiment of the present invention, the oxalic acid solution is prepared in water.

In yet another embodiment of the present invention molybdenum trioxide is added in small quantities to oxalic acid solution maintained at a temperature of 80 to 120° C. to effect complete dissolution of molybdenum trioxide.

In still another embodiment of the present invention the purity of molybdenum trioxide may be at least reagent grade.

In a further embodiment of the present invention the purity of bismuth trioxide may be at least regent grade.

In still further embodiment of the present invention, bismuth hexanoate solution may be mixed to molybdenum hexanoate solution in a ratio such as 2:2 to 2:3.

In another embodiment of the present invention the water used may be such as distilled water, deionised water.

In yet another embodiment of the present invention the precursor solution may have stability of at least three months.

This invention is an improved process for preparing thin film gas detecting element having high ethanol sensitivity. A bismuth molybdate based semiconductor oxide gas detecting element has been found to display a measurable change in electrical resistivity in the presence of ethanol. These changes in electrical resistivity have been found to be reproducible and reversible.

In the present invention known spray pyrolysis technique is used to prepare films of bismuth molybdate on a substrate preferably quartz of dimensions 1 cm×1 cm. The substrate was kept at a temperature in a range of 200 to 300° C. and preferably at a temperature of 200° C. The precursor solution was spayed onto hot substrate by a chemically inert and non-corrosive carrier gas and preferably by nitrogen gas. Subsequent to the deposition of the film the substrate was cooled and the films were subjected to the electrical parameter measurements like variation of resistance with thin film temperature while exposing the film to various concentrations of ethanol vapours. The temperature of the thin film was varied between 250 to 350° C. The variation of resistance may be obtained as a function of time at a given concentration of ethanol vapour. The concentration of ethanol vapour was varied between 10 ppm to 200 ppm. By doing this, the response time of the ethanol sensing thin film was obtained and is defined by the rate of change of resistance from a base initial value. The sensitivity to the ethanol concentration was obtained by exposing the film to a varying quantity of the vapour and measuring at each exposure the change in resistance.

The thin film of the precursor solution is preferably made from a solution of bismuth molybdenum hexanoate solution. This precursor solution may be made by a person skilled in the art to get a solution which upon spray pyrolysed on a substrate at a desired temperature will yield a thin film of any of the three phases of the film namely the α, or β phases of the bismuth molybdate film. The two phases can be obtained by mixing appropriate quantities of bismuth hexanoate and molybdenum hexanoate solutions to get the desired stoichiometric precursor solution. By spray coating the precursor solution, at a substrate temperature of 200 to 300° C. pure alpha or beta phases of bismuth molybdate can be prepared (using the appropriate initial composition) having white, beige colours. From infrared absorption spectra, it was confirmed that the present technique gives pure alpha, beta phases of bismuth molybdate In the present invention for making bismuth molybdate films for ethanol sensing, the precursor solution was made by any of the preferred disclosed methods. Solution of bismuth and molybdenum salts was prepared in an organic medium. The solutions of bismuth and molybdenum prepared in the present invention were such that when the two were mixed together, no precipitation took place unlike the methods disclosed in prior art.

In one of the preferred methods, process developed involves preparation of bismuth molybdenum hexanoate precursor solution through 2-ethyl hexanoic acid route. According to this invention precursor solution is preferably prepared by forming a solution of a bismuth salt preferably bismuth oxide in 2 ethyl hexanoic acid. Suitable bismuth compounds include, but are not limited to bismuth metal when used as a solution with nitric acid, bismuth oxide, bismuth trinitrate pentahydrate and bismuth halides. The other constituent for making the precursor solution involves forming a solution of a molybdenum-containing salt preferably molybdenum oxide also in 2-ethyl hexanoic acid. Suitable molybdenum containing salts may also include molybdenum trioxide, molybdic acid, ammonium molybdates, such as ammonium dimolybdate and ammonium heptamolybdate and molybdenum halides. The two solutions of Bismuth hexonate and molybdenum hexonate are mixed in a proportin so as to give stoichiometrically proportioned precursor solution to have a rartio of Bi to Mo metal in the precursor solution as 2:2 or 2:2 Even though in present process the organic medium for dissolving these salts was hexanoic acid, the process is not limited to this solvent only. The medium for dissolving the salts may also be formic, acetic, caproic, canoic, neodeconic or any other carboxylic acid. The main process details according to a preferred embodimnet, are:

Step 1) $Bi_2O_3$ was dissolved in 2-ethyl hexanoic acid, initially at 120° C. and finally at 200° C.

Step 2) $MoO_3$ was first dissolved in oxalic acid and then molybdenum oxalate was converted to molybdenum hexanoate.

Step 3) The two solutions were mixed together and stirred to get the required precursor solution for spray pyrolysis.

The precursor solution can also be prepared by mixing bismuth hexanoate and molybdenum hexanoate in a proper ratio, by any known method.

In another preferred process for the preparation of the precursor solution, molydenum oxalate solution was prepared by dissolving $MoO_3$ in a minimum quantity of oxalic acid solution in water preferably distilled water. $MoO_3$ was added pinch by pinch to the oxalic acid-water solution while heating at 100° C. When all MoO$_3$ gets dissolved, the clear solution was concentrated. The colour of the solution turns blue at this stage. The 2-ethyl hexanic acid was added to it. The solution was heated at approx 100° C. till the solution is free from water. If excess oxalic acid has been added to dissolve MoO$_3$ in the beginning of the process, then there is bumping in the solution at this stage. Therefore MoO$_3$ has to be dissolved in a minimum quantity of oxalic acid. When the solution is free from water, the solution is further allowed to boil at approx. 200° C. under reflux. The colour of the solution turns brown.

In the second stage of the preferred process, the desired quantity of bismuth oxide is added slowly, pinch by pinch, to the boiling solution of molybdenum hexanoate, under reflux. Bismuth oxide gets dissolved in the solution. The resulting brown coloured solution is ready for making films by spray pyrolysis.

The bismuth molybdate thin film sensor of this invention were tested for changes in its electrical resistance through exposure to varying concentrations of ethanol with the temperature of thin film kept at a temperature in a range from 250° C. to 350° C. For measurement of resistance gold films were evaporated on the thin film to get electrical contact and the distance between the two contacts was 0.025 cms. Contacts were made by attaching copper wires through silver or graphite paste, but better results were obtained with direct pressure contacts. The ethanol response of these thin film sensors was very fast. For example, within 2 seconds of the initial film sensor-gas contact, more than 90% of the resistance change was complete. The steady state was reached within about 5 to 6 sec. With regard to the magnitude of the resistance change, the pure beta phase bismuth molybdate film showed superior performance. Gas sensitivity to very small amounts of vapor (10 ppm ethanol) was attained in all samples. This sensitivity is greater than that seen for most semiconductor gas sensors, primarily because the baseline is relatively stable. Alpha and beta phases of bismuth molybdate samples prepared though above processes gave appreciable change in conductivity when exposed to ethanol vapor and can be used as ethanol sensor elements. Further the variation in sensitivity, with temperature is not as pronounced as in other sensors (SnO$_2$) and a small difference in measurement temperature is tolerable. Hence frequent calibration of temperature is not required.

The invention is particularly directed to a method using change in resistance which can be employed for example to measure the alveolar air of a patient for its alcohol concentration in such a manner that, if necessary, the measuring result can be used for calculating the level of blood alcohol.

The present invention relates generally to the technology of measuring ethanol concentration in air. Heretofore, it has been the conventional belief that the conductivity changes in semiconductor oxide films became large enough to measure only if at least small amounts of a noble metal bearing compound catalyst are added to the semiconductor oxide film material. In the present process the sensor element was shown to show a large change in conductivity/resistivity even when no catalyst (Pt, Pd, etc) are added. However the sensor element would show an improved performance in presence of these catalysts.

The novelty of the present invention lies in eliminating the post deposition anneal.

A further novelty lies in the ability to detect ethanol even at low sensor temperature of 250° C. in contrast to prior art reported temperature of 340° C. The inventive step in the process of preparation lies in the use of precursor solution of bismuth molybdenum hexanoate to prepare the films by known spray pyrolysis without any post deposition anneal.

The following examples are given by way of illustration only and should not be constructed to limit the scope of the present invention.

EXAMPLE-1

Bismuth molybdenum hexanoate precursor solution for preparing α bismuth molybdate film with Bi to Mo ratio of 2:3 was prepared by first dissolving 2.15 gms molybdenum trioxide, in 3 gms of oxalic acid solution made in 50 cc of distilled water. Molybdenum oxide was added in small quantities to the oxalic acid solution maintained at 100° C. The molybdenum oxide was added till all the oxide gets dissolved and then the solution was concentrated by heating till it turns blue. 30 ml of 2 ethyl hexanoic acid was added at a temperature of 120° C. Heating of the solution was continued to 200° C. under reflux thereby giving a brown colour. Next 2.3 gms of bismuth trioxide was added slowly to the resulting brown coloured solution of molybdenum hexanoate under reflux to get homogeneous mixed precursor solution of dark brown colour.

EXAMPLE-2

The bismuth molybdenum hexanoate precursor solution of Example 1 was used to prepare a thin film ethanol sensor of α bismuth molybdate with Bi to Mo ratio of 2:3. The thin film was prepared by spraying the solution by means of Nitrogen carrier gas on quartz substrate held at 300° C. The size of quartz substrate was 1 cm×1 cm. On this thin film so formed, gold contact electrodes were deposited by vacuum thermal evaporation. Electrical conducting wires attached to the gold electrodes by pressure contacts. Resistance of α bismuth molybdate thin film was measured first in air $R_0$ at a sensor temperature of 275° C. Next the resistance $R_g$ of the thin film ethanol sensor was measured at a sensor temperature of 275° C. for ethanol vapour concentrations varying between 20 to 100 ppm. The sensitivity of the sensor to ethanol detection was determined by calculating the ratio ($R_0/R_g$). The sensitivity of the α bismuth molybdate thin film was 2.1, 4, 6 for 25, 50 and 100 ppm ethanol vapour respectively.

EXAMPLE-3

The bismuth molybdenum hexanoate precursor solution of Example 1 was used to prepare a thin film ethanol sensor of α bismuth molybdate with Bi to Mo ratio of 2:3. The thin film was prepared by spraying the solution by means of Nitrogen carrier gas on quartz substrate held at 300° C. The size of quartz substrate was 1 cm×1 cm. On this thin film so formed, gold contact electrodes were deposited by vacuum thermal evaporation. Electrical conducting wires attached to the gold electrodes by pressure contacts. Resistance of α bismuth molybdate thin film was measured first in air $R_0$. Next the resistance $R_g$ of the thin film ethanol sensor was measured at a sensor temperature of 300° C. for ethanol vapour concentrations varying between 20 to 100 ppm. The sensitivity of the sensor to ethanol detection was determined by calculating the ratio ($R_0/R_g$). The sensitivity of the a bismuth molybdate thin film was 3.2, 4.5, 7 for 25, 50 and 100 ppm ethanol vapour respectively.

EXAMPLE-4

The bismuth molybdenum hexanoate precursor solution of Example 1 was used to prepare a thin film ethanol sensor of α bismuth molybdate with Bi to Mo ratio of 2:3. The thin film was prepared by spraying the solution by means of Nitrogen carrier gas on quartz substrate held at 300° C. The size of quartz substrate was 1 cm×1 cm. On this thin film so formed, gold contact electrodes were deposited by vacuum thermal evaporation. Electrical conducting wires attached to the gold electrodes by pressure contacts. Resistance of α bismuth molybdate thin film was measured first in air $R_0$. Next the resistance $R_g$ of the thin film ethanol sensor was measured at a sensor temperature of 325° C. for ethanol vapour concentrations varying between 20 to 100 ppm. The sensitivity of the sensor to ethanol detection was determined by calculating the ratio ($R_0/R_g$). The sensitivity of the α bismuth molybdate thin film was 2.6, 4.3, 6.4, 8.9 and 13 for 10, 25, 50, 100 and 250 ppm ethanol vapour respectively.

EXAMPLE-5

The bismuth molybdenum hexanoate precursor solution of Example 1 was used to prepare a thin film ethanol sensor of α bismuth molybdate with Bi to Mo ratio of 2:3. The thin film was prepared by spraying the solution by means of Nitrogen carrier gas on quartz substrate held at 300° C. The size of quartz substrate was 1 cm×1 cm. On this thin film so formed, gold contact electrodes were deposited by vacuum thermal evaporation. Electrical conducting wires attached to the gold electrodes by pressure contacts. Resistance of α bismuth molybdate thin film was measured first in air $R_0$ and next $R_g$ in ethanol vapour concentration 100 ppm at various temperatures from 250–325 C. The sensitivity of the sensor to ethanol detection was determined by calculating the ratio ($R_0/R_g$). The sensitivity of the α bismuth molybdate thin film was 2.4, 4, 5.7, 6.5, 7, 7.6 and 9 for 250, 275, 300, 315, 325 and 340° C. respectively.

EXAMPLE-6

Bismuth molybdenum hexanoate precursor solution for preparing thin film of β bismuth molybdate with Bi to Mo ratio of 2:2 was prepared by first dissolving 1.45 gms molybdenum trioxide in 3 gms of oxalic acid solution made in 50 ml of distilled water. Molybdenum oxide was added in small quantities to the oxalic acid solution maintained at 100° C. The molybdenum oxide was added till all the oxide gets dissolved. The solution was concentrated by heating till it turns blue. 30 ml of 2 ethyl hexanoic acid was added at a temperature of 120° C. Heating of the solution was continued to 200° C. under reflux thereby giving a brown coloured solution. Next 2.35 gms of bismuth trioxide was added slowly to the resulting brown solution of molybdenum hexanoate under reflux to get homogeneous mixed precursor solution of dark brown colour.

EXAMPLE-7

The bismuth molybdenum hexanoate precursor solution of Example 5 was used to prepare a thin film ethanol sensor of β bismuth molybdate with Bi to Mo ratio of 2:2. The thin film was prepared by spraying the solution by means of Nitrogen carrier gas on quartz substrate held at 250° C. The size of quartz substrate was 1 cm×1 cm. On this thin film so formed, gold contact electrodes were deposited by vacuum thermal evaporation. Electrical conducting wires were attached to the gold electrodes by pressure contacts. Resistance of β bismuth molybdate thin film was measured first in air $R_0$ at a sensor temperature of 275° C. Next the resistance $R_g$ of the thin film ethanol sensor was measured at a sensor temperature of 275° C. for ethanol vapour concentrations varying between 20 to 100 ppm. The sensitivity of the sensor to ethanol detection was determined by calculating the ratio ($R_0/R_g$). The sensitivity of the β bismuth molybdate thin film was 2.6, 4 and 7.7 for 10, 20 and 100 ppm ethanol vapour respectively.

EXAMPLE-8

The bismuth molybdenum hexanoate precursor solution of Example 5 was used to prepare a thin film ethanol sensor of β bismuth molybdate with Bi to Mo ratio of 2:2. The thin film was prepared by spraying the solution by means of Nitrogen carrier gas on quartz substrate held at 250° C. The size of quartz substrate was 1 cm×1 cm. On this thin film so formed, gold contact electrodes were deposited by vacuum thermal evaporation. Electrical conducting wires attached to the gold electrodes by pressure contacts. Resistance of β bismuth molybdate thin film was measured first in air $R_0$ at a sensor temperature of 300° C. Next the resistance $R_g$ of the thin film ethanol sensor was measured at a sensor temperature of 300° C. for ethanol vapour concentrations varying between 20 to 100 ppm. The sensitivity of the sensor to ethanol detection was determined by calculating the ratio ($R_0/R_g$). The sensitivity of the β bismuth molybdate thin film was 4.1, 5.2, 6.6 and 8.5 for 10, 25, 50 and 100 ppm ethanol vapour respectively.

EXAMPLE-9

The bismuth molybdenum hexanoate precursor solution of Example 5 was used to prepare a thin film ethanol sensor of β bismuth molybdate with Bi to Mo ratio of 2:2. The thin film was prepared by spraying the solution by means of Nitrogen carrier gas on quartz substrate held at 250° C. The size of quartz substrate was 1 cm×1 cm. On this thin film so formed, gold contact electrodes were deposited by vacuum thermal evaporation. Electrical conducting wires attached to the gold electrodes by pressure contacts. Resistance of β bismuth molybdate thin film was measured first in air $R_0$ at a sensor temperature of 325° C. Next the resistance $R_g$ of the thin film ethanol sensor was measured at a sensor temperature of 325° C. for ethanol vapour concentrations varying between 20 to 100 ppm. The sensitivity of the sensor to ethanol detection was determined by calculating the ratio ($R_0/R_g$). The sensitivity of the β bismuth molybdate thin film was 4.5, 7.7, 9.4, 12.6 and 10, 50, 100, 200, 300 and 600 ppm ethanol vapour respectively.

Some of the experiments done in respect of the novel ethanol sensor of the invention is captured in the tables herebelow wherein, Tables 1 and Tables 2 depict the sensitivity of the thin film to ethanol vapour. The phase of the thin film in Tables 1 is alpha whereas the phase is beta in table 2.

TABLE 1

| S. NO. | PHASE OF THIN FILM SENSOR | SENSOR TEMP. IN ° C. | VAPOUR CONCENTRATION IN ppm | SENSITIVITY |
|---|---|---|---|---|
| 1. | Alpha | 275 | 25 | 2.1 |
|  |  |  | 50 | 4 |
|  |  |  | 100 | 6 |
| 2. | Alpha | 300 | 25 | 3.2 |
|  |  |  | 50 | 4.5 |
|  |  |  | 100 | 7.0 |
| 3. | Alpha | 325 | 10 | 2.6 |
|  |  |  | 25 | 4.3 |
|  |  |  | 50 | 6.4 |
|  |  |  | 100 | 8.9 |
|  |  |  | 250 | 13 |

TABLE 2

| S. NO. | PHASE OF THIN FILM SENSOR | SENSOR TEMP. IN °C. | VAPOUR CONCENTRATION IN ppm | SENSITIVITY |
|---|---|---|---|---|
| 1. | Beta | 275 | 10 | 2.6 |
|  |  |  | 20 | 4 |
|  |  |  | 100 | 7.7 |
| 2. | Beta | 300 | 10 | 4.1 |
|  |  |  | 25 | 5.2 |
|  |  |  | 50 | 6.6 |
|  |  |  | 100 | 8.5 |
| 3. | Beta | 325 | 10 | 4.5 |
|  |  |  | 50 | 7.7 |
|  |  |  | 100 | 9.4 |
|  |  |  | 200 | 12.6 |
|  |  |  | 300 | 14.2 |

Table 3 shows the stability data for α-bismuth molybdate film when tested at 300° C. for 1 year. As the table shows, the films are quite adherent and stable with time. The sensitivity does not change since it is not affected by atmosphere humidity. Even if there is slight change in the room temperature resistance, the sensitivity remains almost same. Further if there is large change in room temperature resistance it can be restored by keeping the sample heated at 300° C. till the resistance resumes to original value.

TABLE 3

Stability data for α-bismuth molybdate film (100 ppm ethanol/300° C.)

| Time | Sensitivity |
|---|---|
| After 1-day | 6.97 |
| After 7-days | 7.04 |
| After 1 month | 6.95 |
| After 3 months | 6.93 |
| After 6 months | 7.08 |
| After 1 year | 7.1 |

The main advantages of the present invention are:
1. The precursor solution can be made at low cost.
2. The precursor material is very stable and has a long shelf life.
3. The thin film of bismuth molybdate does not need any post deposition heat treatment.
4. The ethanol sensing can be achieved in a short time interval of 10 seconds.

What is claimed is:

1. A process for preparation of a sensitive, fast response thin film ethanol sensor said process comprises dissolving molybdenum trioxide in oxalic acid solution, the said solution being concentrated to give a blue colored solution, adding 2-ethyl hexanoic acid to said blue colored solution, heating the resulting mixed solution to a temperature in the range of 100 to 150° C. for a period in the range of 30–60 minutes to remove water, the said water free solution being maintained at a temperature in the range of 150 to 200° C. for a period in the range of 30–90 minutes to obtain a hot brown colored solution, adding bismuth trioxide slowly to the said brown colored hot solution under reflux, thereby obtaining bismuth molybdenum precursor solution, depositing a thin film of the said precursor solution on a substrate at a temperature in the range of 200 to 400° C., cooling the deposited film, depositing electrode contacts on the said thin film ethanol sensor.

2. A process for preparing precursor solution of bismuth molybdenum hexanoate said process comprising: dissolving molybdenum trioxide in oxalic acid solution, the said solution being concentrated to give a blue coloured solution, adding 2-ethyl hexanoic acid to said blue coloured solution, heating the resulting mixed solution to a temperature in the range of 100 to 150° C. for a period in the range of 30 to 60 minutes to remove water, said water free solution being maintained at a temperature in the range of 150 to 250° C. for a period in the range of 30 to 90 minutes to obtain a hot brown coloured solution, adding bismuth trioxide slowly to the said brown coloured hot solution under reflux thereby getting bismuth molybdenum hexanoate precursor solution.

3. A process as claimed in claim 2, wherein the purity of 2 ethyl hexanoic acid may be at least reagent grade.

4. A process as claimed in claim 2, wherein the oxalic acid solution is prepared in water.

5. A process as claimed in claim 2, wherein molybdenum trioxide is added in small quantities to oxalic acid solution maintained at a temperature of 80 to 120° C. to effect complete dissolution of molybdenum trioxide.

6. A process as claimed in claim 2, wherein the purity of molybdenum trioxide may be at least reagent grade.

7. A process as claimed in claim 2, wherein the purity of bismuth trioxide may be at least regent grade.

8. A process as claimed in claim 2, wherein bismuth hexanoate solution may be mixed to molybdenum hexanoate solution in a ratio such as 2:2 to 2:3.

9. A process as claimed in claim 2, wherein the water used may be such as distilled water, deionised water.

10. A process as claimed in claim 2, wherein the precursor solution may have stability of at least three months.

* * * * *